(12) United States Patent
Weed et al.

(10) Patent No.: US 10,849,581 B2
(45) Date of Patent: Dec. 1, 2020

(54) ADJUSTABLE GUIDE WHEEL FOR AXIAL POSITIONING OF A ROTATABLE GANTRY OF AN IMAGING MODALITY

(71) Applicant: ANALOGIC CORPORATION, Peabody, MA (US)

(72) Inventors: Steven D. Weed, Marblehead, MA (US); Andrew Alvino, Haverhill, MA (US)

(73) Assignee: Analogic Corporation, Peabody, MA (US)

( * ) Notice: Subject to any disclaimer, the term of this patent is extended or adjusted under 35 U.S.C. 154(b) by 81 days.

(21) Appl. No.: 16/033,366

(22) Filed: Jul. 12, 2018

(65) Prior Publication Data

US 2020/0020460 A1    Jan. 16, 2020

(51) Int. Cl.
| | |
|---|---|
| *A61B 6/00* | (2006.01) |
| *A61B 6/03* | (2006.01) |
| *G01V 5/00* | (2006.01) |
| *G01N 23/046* | (2018.01) |

(52) U.S. Cl.
CPC ............ *A61B 6/4435* (2013.01); *A61B 6/035* (2013.01); *G01N 23/046* (2013.01); *G01V 5/005* (2013.01)

(58) Field of Classification Search
CPC .... A61B 6/035; A61B 6/4435; G01N 23/046; G01V 5/005
See application file for complete search history.

(56) References Cited

U.S. PATENT DOCUMENTS

| | | | |
|---|---|---|---|
| 2012/0148013 A1* | 6/2012 | Zhang ..................... | A61B 6/03 378/4 |
| 2014/0119515 A1* | 5/2014 | McKenna ................ | A61B 6/44 378/197 |

FOREIGN PATENT DOCUMENTS

WO    WO-2018190867 A1 * 10/2018 ............. A61B 6/035

* cited by examiner

*Primary Examiner* — Chih-Cheng Kao
(74) *Attorney, Agent, or Firm* — TraskBritt

(57) ABSTRACT

Among other things, a guide unit and a radiation system including a guide unit are provided. The guide unit limits axial movement of a rotatable structure supporting a radiation source and a detector array of the radiation system. Embodiments of the guide unit include a frame member configured to be supported by a stationary unit that forms a portion of the radiation system. A guide wheel coupled to the frame member is configured to roll along a periphery of the rotatable structure of the radiation system as the rotatable structure supporting the radiation source and the detector array is rotated about an axis of rotation during operation of the radiation system. A wheel adjustment system coupled to the frame member linearly translates the guide wheel toward the periphery of the rotatable structure supported by the stationary unit of the radiation system.

22 Claims, 5 Drawing Sheets

ADJUSTABLE GUIDE WHEEL FOR AXIAL POSITIONING OF A ROTATABLE GANTRY OF AN IMAGING MODALITY

TECHNICAL FIELD

The present disclosure relates to a guide unit for limiting axial movement of a rotatable structure supporting a radiation source and a detector array of a radiation system. The guide unit finds particular application in the context of computed tomography (CT) scanners, but the features described herein are not intended to be limited to CT applications and/or other radiation imaging applications.

BACKGROUND

Today, CT and other radiation imaging modalities (e.g., mammography, digital radiography, single-photon emission computed tomography, etc.) are useful to provide information, or images, of interior aspects of an object under examination. Generally, the object is exposed to radiation (e.g., X-rays, gamma rays, etc.), and an image(s) is formed based upon the radiation absorbed and/or attenuated by the interior aspects of the object, or rather an amount of radiation photons that is able to pass through the object. Typically, highly dense aspects of the object (or aspects of the object having a composition comprised of higher atomic number elements) absorb and/or attenuate more radiation than less dense aspects, and thus an aspect having a higher density (and/or high atomic number elements), such as a bone or metal, for example, will be apparent when surrounded by less dense aspects, such as muscle or clothing.

Radiation imaging modalities generally comprise, among other things, one or more radiation sources (e.g., an X-ray source, Gamma-ray source, etc.) and a detector array comprised of a plurality of pixels or detector cells that are respectively configured to convert radiation that has traversed the object into signals that may be processed to produce the image(s). As an object is passed between the radiation source(s) and the detector array, radiation is absorbed/attenuated by the object, causing changes in the amount/energy of detected radiation. Using information derived from the detected radiation, radiation imaging modalities are configured to generate images that can be used to detect items within the object that may be of particular interest (e.g., body characteristics, threat items, etc.). These images may be two-dimensional images or three-dimensional images.

To generate three-dimensional images, at least one of the radiation source(s) or the detector array are rotated relative to the object under examination to acquire information about the object from various views. In CT scanners, the radiation source(s) and the detector array are typically mounted to a rotatable structure (e.g., a disk or drum) that is rotated about the object under examination. The rotatable structure must be sized to accommodate the object (e.g., luggage, a human patient, etc.) in a center bore, and thus the outer diameter of such disks or drums may exceed five feet.

Three-dimensional images can be generated of elongated portions of the object by acquiring information about separate individual regions. The information acquired for each individual region is commonly referred to as a "slice" of the object. After the information for a slice is acquired, the relative positioning of the object and rotatable structure along an axial direction of the rotatable structure is adjusted to align the region of interest for the next slice with the radiation source and detector array. The acquired slices are assembled into a composite image of the elongated portion of the object that is of interest.

To accurately capture information for the object regions of interest, imaging systems such as CT scanners require very accurate rotatable structure positioning in the axial direction for successful operation. However, manufacturing tolerances, inconsistencies inherent to installation and assembly processes, as well as departures of the CT scanners from their installed configuration resulting from "wear-and-tear" after prolonged usage can negatively affect the axial alignment of the rotatable structure. If the imaging accuracy of such CT scanners becomes unacceptable for diagnostic purposes, a service provider must perform maintenance of the CT scanners on-site. Such maintenance has traditionally involved the complete removal and replacement of a mechanical restraint that fixes the axial position of the rotatable structure, which is laborious and expensive, and causes significant downtime of the CT scanners.

More recently, an eccentric cam has been included as part of the mechanical restraint that establishes the axial position of the rotatable structure. A roller is supported by an eccentrically-mounted hub, which has an off-center axis of rotation. Rotation of the hub about its axis of rotation not only adjusts the position of the hub relative to the rotatable structure, but also necessarily causes tangential displacement of the roller relative to the rotatable structure. The tangential displacement is unpredictable because it depends on the extent of adjustment required, which varies by installation based on the "look-and-feel" of the installer. As a result, significant unexpected forces are often imposed on components of the CT scanners such as the bearings of the mechanical restraint, thereby shortening the life of such components and adding to the maintenance costs and downtime of the CT scanners.

BRIEF SUMMARY

Aspects of the present disclosure address the above matters, and others. According to one aspect a guide unit for limiting axial movement of a rotatable structure supporting a radiation source and a detector array of a radiation system is provided. The guide unit includes a frame member configured to be supported by a stationary unit that forms a portion of the radiation system. A guide wheel coupled to the frame member is configured to roll along a periphery of the rotatable structure of the radiation system as the rotatable structure supporting the radiation source and the detector array is rotated about an axis of rotation during operation of the radiation system. A wheel adjustment system linearly translates the guide wheel relative to the frame member toward the periphery of the rotatable structure supported by the stationary unit of the radiation system.

According to another aspect, radiation system is provided. The radiation system includes a stationary unit, and a rotatable structure configured for rotation about an axis of rotation relative to the stationary unit. The rotatable structure includes at least: (i) a cylindrical body extending in an axial direction along the axis of rotation to define an interior passage, and (ii) a peripheral surface at a terminal end of the cylindrical body. The peripheral surface defines an aperture leading into the interior passage defined by the cylindrical body. A radiation source and a detector array are mounted to the rotatable structure. A rotatable support mechanism is configured to at least partially support and facilitate the rotation of the rotatable unit about the axis of rotation. The radiation system also includes a guide unit for limiting axial movement of the rotatable structure. The guide unit includes a frame member configured to be coupled to the stationary unit, and a guide wheel coupled to the frame member. The guide wheel is configured to roll along the peripheral surface of the rotatable structure as the rotatable structure is rotated about the axis of rotation during operation of the radiation system. A wheel adjustment system linearly translates the guide wheel relative to the frame member toward the peripheral surface of the rotatable structure supported by the stationary unit of the radiation system.

According to another aspect, a method involves limiting axial movement of a rotatable structure supporting a radiation source and a detector array of a radiation system. The method includes, while a surface of a guide wheel is positioned adjacent to a peripheral surface of a cylindrical body that forms a portion of the rotatable structure, manipulating an adjustment member provided to a wheel adjustment system to cause linear translation of the surface of the guide wheel toward the peripheral surface of the cylindrical body. The adjustment member manipulated is accessible externally of a frame member supporting the guide wheel without requiring disassembly of the frame member. After manipulating the adjustment member to cause the linear translation of the surface of the guide wheel, a locking device is operated to interfere with further linear translation of the guide wheel away from the peripheral surface of the cylindrical body. The locking device includes a member that extends through a portion of the frame member and engages a portion of the wheel adjustment system to interfere with further linear translation of the guide wheel.

Those of ordinary skill in the art will appreciate still other aspects of the present application upon reading and understanding the appended description.

BRIEF DESCRIPTION OF THE DRAWINGS

This disclosure is illustrated by way of example and not limitation in the figures of the accompanying drawings, in which like references generally indicate similar elements and in which.

DETAILED DESCRIPTION

Figure 1:
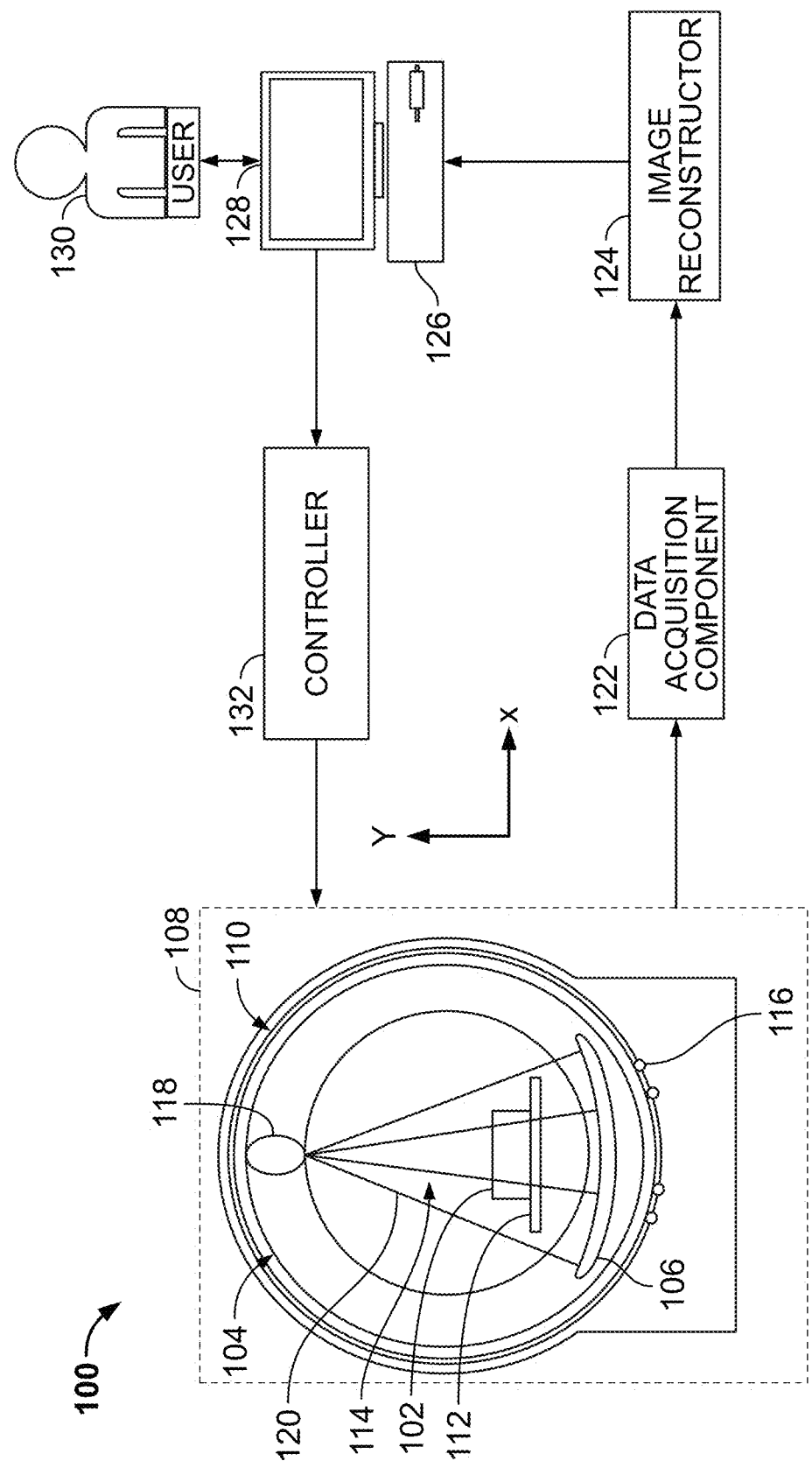
FIG. 1 is a schematic view of an illustrative example of an imaging modality.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a guide unit for limiting axial movement of a rotatable structure supporting a radiation source and a detector array of a radiation system, and a radiation system including such a guide unit. The guide unit includes a frame member configured to be supported by a stationary unit that forms a portion of the radiation system. A guide wheel is coupled to the frame member, and is configured to roll along a periphery of the rotatable structure of the radiation system as the rotatable structure supporting the radiation source and the detector array is rotated about an axis of rotation during operation of the radiation system. A wheel adjustment system can be manipulated to cause linear translation of the guide wheel relative to the frame member, in a direction toward the periphery of the rotatable structure supported by the stationary unit of the radiation system.

Embodiments of the wheel adjustment system can optionally limit, or constrain, the linear translation of the guide wheel to translations only in an axial direction of the rotatable structure of the radiation system. For example, the wheel adjustment system can include a track defining a linear path along which a hub supporting the guide wheel can travel. For example, the track can include a threaded shaft supported by a portion of the frame member. Compatible threading provided to a portion of the hub can threadedly engage threading provided to the threaded shaft. A gear system, such as a worm drive, for example, can convert an angular force input by a user into a rotational force that causes pivotal adjustment of the threaded shaft. Cooperation between the threading provided to the threaded shaft and the portion of the hub causes the hub to travel along the linear path defined by the threaded shaft. Of course other embodiments can utilize a linear track such as a rack-and-pinion arrangement, or any other device that allows fine, incremental or continuous linear translation of the guide wheel generally toward a peripheral surface of the rotating structure supporting the radiation source and/or sensor array.

Further, some embodiments of the linear path defined by the wheel adjustment system can be substantially orthogonal to the peripheral surface. For example, the linear path can be substantially parallel with the axis of rotation of the rotatable structure. Thus, the linear path can be parallel with the rotational axis of the rotatable structure, or at least within an acceptable tolerance of a parallel alignment for purposes of improving the repeatability of compressing the guide wheel against the same region of the peripheral surface. For some embodiments, the acceptable tolerance can allow an axis of the linear path to form an acute angle with the axis of rotation of the rotatable structure, such as an angle of up to 20°, or up to 15°, or up to 10°, or up to 5° from the rotational axis of the rotatable structure.

According to some embodiments, at least a portion of the wheel adjustment system can be disposed within an aperture formed in the frame member. An access channel can be formed in the frame member to extend between the aperture and an exterior of the frame member. The access channel receives an adjustment member that imparts the angular input force on the worm while protruding externally of the frame member. For example, the adjustment member can include an elongated post having a distal end coupled to a worm that can be pivoted to impart a rotational force on a worm gear. A proximate end of the post can protrude from the frame member, allowing a user to apply an angular input force on the post, causing pivotal adjustment of the worm. For some embodiments, however, the adjustment member received within the access channel can be a portion of a separate tool such as a screwdriver, a polygon key (e.g., a "hex key"), or other such elongated tool, for example.

In use, the guide wheel can be roughly positioned adjacent to the peripheral surface of the rotatable structure as a result of installation of the frame member on the stationary unit. A user can apply an angular input force onto the adjustment member protruding externally of the frame member, allowing fine adjustment of the guide wheel position through linear translation, without requiring disassembly of the frame member. Pivoting, rotating or otherwise manipulating the adjustment member causes linear translation of a hub supporting the guide wheel, and accordingly, the guide wheel, toward the peripheral surface of the rotatable structure. According to some embodiments, the adjustment member can be manipulated an extent suitable to cause compression of the surface of the guide wheel up to two (0.02 in.) hundredths of an inch, or up to one (0.01 in.) hundredth of an inch, for example, against the peripheral surface of the cylindrical body. For some embodiments, the adjustment member can be manipulated to cause linear translation of the guide wheel a distance up to one half (0.5 in.) of an inch, or up to one quarter (0.25 in.) of an inch, for example.

Once the guide wheel has been positioned via linear translation, a locking device extending through a portion of the frame member can be manipulated by the user to interfere with further linear translation of the guide wheel, toward or away from the peripheral surface. Similar to the wheel adjustment system, the locking device can be accessible to be manipulated externally of the frame member, without requiring disassembly of the frame member, or separation of the frame member from the stationary unit. When manipulated, the locking device engages a portion of the wheel adjustment system, and interferes with further linear translation of the guide wheel. For example, the locking device can include a set screw that is screwed into a threaded aperture of the frame member to make contact with a portion of the wheel adjustment system. According to some embodiments, the set screw can be inserted to make contact with a threaded shaft, thereby creating a friction fit that interferes with pivotal adjustment of the threaded shaft. The contact between the set screw, and optionally cooperation between components of the wheel adjustment system (e.g., a worm and a worm gear) can resist a reactionary force urging the guide wheel in a linear direction away from the peripheral surface. For example, the reactionary force generated as a result of contact between the guide wheel and the peripheral surface can be resisted, thereby maintaining a position of the guide wheel against the peripheral surface.

Accordingly, the linear translation of the guide wheel by the wheel adjustment system allows for a precise, and repeatable axial alignment of the rotatable structure of the radiation system. The accurate axial alignment of the rotatable structure improves the ability of the CT scanner or other applicable imaging modality to accurately acquire information to generate images at specific locations of the object. Further, establishing contact between the guide wheel and the peripheral surface of the rotatable object at a known location along the peripheral surface, without having to take into account tangential movement of the guide wheel, improves the life of components forming portions of the guide unit.

With reference to the drawings, FIG. 1 shows an illustrative example of an environment 100 comprising an embodiment of a radiation imaging modality (e.g., radiation system) that may be configured to generate data (e.g., images) representative of an object 102 or aspect(s) thereof under examination. It will be appreciated that the features described herein may find applicability to other imaging modalities besides the illustrative computed tomography (CT) scanner illustrated in FIG. 1. For example, a rotatable structure 104 described herein may find applicability to other types of radiation imaging modalities, such as SPECT scanners. Moreover, the arrangement of components and/or the types of components included in the illustrative environment 100 are for illustrative purposes only. For example, the rotatable structure 104 (e.g., a rotating gantry) may comprise additional components to support the operation of a radiation source 118 and/or detector array 106, such as a cooling unit, power units, etc. As another example, at least a portion of a data acquisition component 122 may be comprised within and/or attached to the detector array 106.

In the illustrative environment 100, an examination unit 108 of the imaging modality is configured to examine one or more objects 102. The examination unit 108 can comprise a rotatable structure 104 and a stationary unit 110, which may encase and/or surround as least a portion of the rotatable structure 104 (e.g., as illustrated with an outer, stationary ring, surrounding an outside edge of an inner, rotating ring). During an examination of the object(s) 102, the object(s) 102 can be placed on an object support 112, such as a bed or conveyor belt, for example, that is selectively positioned in an examination region 114 (e.g., a hollow bore in the rotatable structure 104), and the rotatable structure 104 can be rotated and/or supported about the object(s) 102 by a rotator 116, such as a bearing, motor, belt wheel unit, drive shaft, chain, roller truck, etc.

The rotatable structure 104 may by substantially cylindrical in shape, and surround a portion of the examination region 114. The rotatable structure may comprise one or more radiation sources 118 (e.g., an ionizing X-ray source, gamma radiation source, etc.) and a detector array 106 that is mounted on a substantially diametrically opposite side of the rotatable structure 104 relative to the radiation source(s) 118.

During an examination of the object(s) 102, the radiation source(s) 118 emits fan or cone shaped radiation 120 configurations from a focal spot(s) of the radiation source(s) 118 (e.g., a region within the radiation source(s) 118 from which radiation 120 emanates) into the examination region 114. It will be appreciated that such radiation 120 may be emitted substantially continuously and/or may be emitted intermittently (e.g., a brief pulse of radiation is emitted followed by a resting period during which the radiation source 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 can comprise a linear (e.g., one-dimensional) or two-dimensional array of elements (sometimes referred to as pixels, channels, or detector cells) disposed as a single row or multiple rows in the shape of spherical arc, typically having a center of curvature at the focal spot of the radiation source(s) 118, for example. As the rotatable structure 104 rotates, the detector array 106 is configured to directly convert (e.g., using amorphous selenium and/or other direct conversion materials) and/or indirectly convert (e.g., using Cesium Iodide (CsI) and/or other indirect conversion materials) detected radiation into electrical signals.

Signals that are produced by the detector array 106 may be transmitted to a data acquisition component 122 that is in operable communication with the detector array 106. Typically, the data acquisition component 122 is configured to convert the electrical signals output by the detector array 106 into digital data and/or to combine the digital data acquired during a measuring interval. The collection of digital output signals for a measuring interval may be referred to as a "projection" or a "view."

The illustrative environment 100 also illustrates an image reconstructor 124 that is operably coupled to the data acquisition component 122 and is configured to generate one or more images representative of the object 102 under examination based at least in part upon signals output from the data acquisition component 122 using suitable analytical, iterative, and/or other reconstruction technique (e.g., tomosynthesis reconstruction, back-projection, iterative reconstruction, etc.).

The illustrative environment 100 also includes a terminal 126, or workstation (e.g., a computer), configured to receive image(s) from the image reconstructor 124, which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input which can direct operations of the object examination unit 108 (e.g., a speed of rotation for the rotatable structure 104, an energy level of the radiation, etc.).

In the illustrative environment 100, a controller 132 is operably coupled to the terminal 126. In one example, the controller 132 is configured to receive user input from the terminal 126 and generate instructions for the examination unit 108 indicative of operations to be performed.

It will be appreciated that the component diagram is merely intended to illustrate one embodiment of one type of imaging modality and is not intended to be interpreted in a limiting manner. For example, the functions of one or more components described herein may be separated into a plurality of components and/or the functions of two or more components described herein may be consolidated into merely a single component. Moreover, the imaging modality may comprise additional components to perform additional features, functions, etc. (e.g., such as automatic threat detection).

Figure 2:
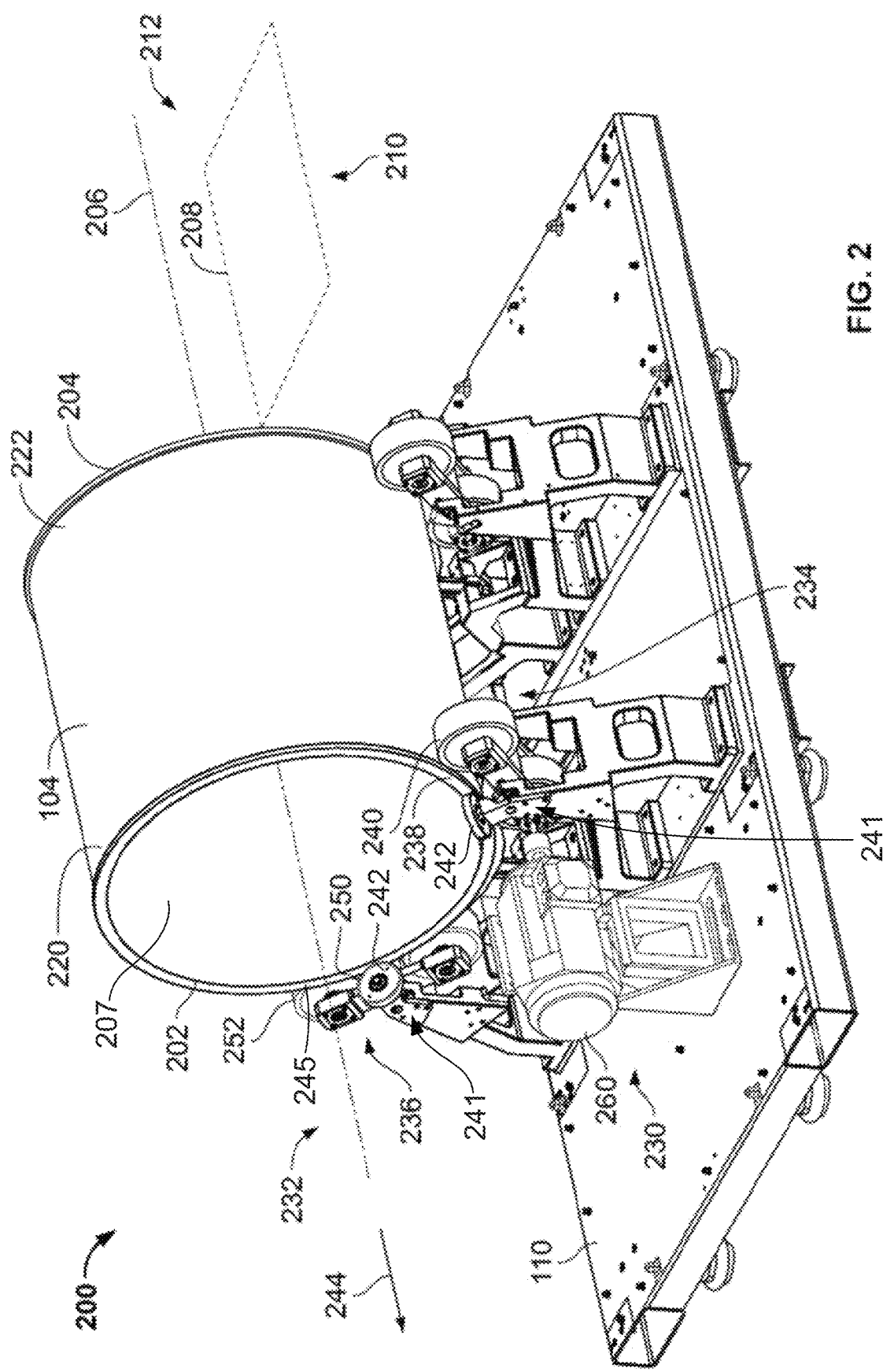
FIG. 2 is a partially-cutaway view of an illustrative embodiment of a radiation system having a stationary unit and a rotatable structure.

FIG. 2 depicts an illustrative embodiment of a radiation system 200 (e.g., examination unit 108) that can be used within the environment 100 of FIG. 1. In an example, the radiation system 200 comprises the rotatable structure 104 and the stationary unit 110. The rotatable structure 104 can extend between a first end 202 and a second end 204 along a rotation of axis 206. For some embodiments, with the radiation source 118 and the detector array 106 mounted to the rotatable structure 104, the rotatable structure 104 is configured to rotate about the axis 206 relative to the stationary unit 110.

The axis 206 may lie within a plane 208 that bisects the rotatable structure 104. In an example, the plane 208 can extend substantially parallel to a major plane of the stationary unit 110 and/or to a surface upon which the radiation system 200 rests. In this way, the plane 208 can define a first side 210 and a second side 212, wherein the first side 210 comprises a bottom portion (e.g., a bottom half) of the rotatable structure 104 while the second side 212 comprises a top portion (e.g., a top half) of the rotatable structure 104.

The rotatable structure 104 can comprise one or more rotational surfaces, such as a first rotational surface 220 extending about the axis 206 and a second rotational surface 222 extending about the axis 206. In an example, the first rotational surface 220 and the second rotational surface 222 can be defined at an outer radial side of the rotatable structure 104. The first rotational surface 220 and the second rotational surface 222 can extend substantially circularly (e.g., by having a circular shape) about the axis 206. In an example, the first rotational surface 220 may be disposed adjacent to the first end 202 of the rotatable structure 104, while the second rotational surface 222 may be disposed adjacent to the second end 204 of the rotatable structure 104. The first rotational surface 220 and the second rotational surface 222 can define a substantially smooth outer surface about the axis 206.

The radiation system 200 comprises a wheel unit 230, interchangeably referred to herein as a rotatable support mechanism, configured to support and/or facilitate rotation of the rotatable structure 104. In an example, the wheel unit 230 comprises a wheel mechanism set 232. The wheel mechanism set 232 is configured to at least partially support the rotatable structure 104 at the first rotational surface 220 and facilitate rotation of the rotatable structure 104 relative to the stationary unit 110. In an example, the wheel mechanism set 232 can be supported by and/or attached to the stationary unit 110. The wheel mechanism set 232 can be positioned adjacent to the first end 202 of the rotatable structure 104.

The wheel mechanism set 232 comprises a wheel mechanism 234 and a second wheel mechanism 236. The wheel mechanism 234 is configured to at least partially support the rotatable structure 104 and facilitate rotation of the rotatable structure 104 relative to the stationary unit 110. In an example, the wheel mechanism 234 can rotationally support the rotatable structure 104 at a first location 238 of the first rotational surface 220, with the first location 238 lying on the first side 210 of the plane 208. In this way, the wheel mechanism 234 can contact the bottom portion of the rotatable structure 104 (e.g., an axial face), with the rotatable structure 104 resting upon the wheel mechanism 234 due to the force of gravity.

By way of example, the wheel mechanism 234 comprises at least one roller 240 that is configured to support and/or impart a rotation-driving force onto the rotatable structure 104, causing rotation of the rotatable structure about the axis 206. The wheel mechanism 234, or any other portion of the wheel unit, can also include a guide unit 241 coupled thereto for limiting axial movement of the rotatable structure 104 in an axial direction along the axis 206. The guide unit 241 may be separable from, and configured to be installed on the wheel mechanism 234 or other structure coupling the guide unit 241 to the stationary unit 110, but can also be integrally formed as a monolithic structure as part of the wheel mechanism 234 or other component. The guide unit 241 includes a guide wheel 242 that is oriented substantially perpendicular to the at least one roller 240. The guide wheel 242 can contact and/or engage a peripheral surface 245 at the first end 202 in an axial direction 244 of the rotatable structure 104 along the axis 206. The peripheral surface 245 defines an aperture leading into an interior passage 207 defined by the cylindrical body of the rotatable structure 104. Embodiments of the peripheral surface 245 can include a substantially planar surface, formed as a flange extending substantially-perpendicularly away from an external, cylindrical surface of the rotatable structure 104. In this way, the guide wheel 242 can limit movement of the rotatable structure 104 along the axis 206. For example, the guide wheel 242 can make contact with, and optionally be pressed against the peripheral surface 245, to limit unintended movement of the rotatable structure 104 along the first, axial direction 244 that is substantially parallel to the axis 206 as described in detail below.

The second wheel mechanism 236 is configured to at least partially support the rotatable structure 104 and facilitate rotation of the rotatable structure 104 relative to the stationary unit 110. In an example, the second wheel mechanism 236 can rotationally support the rotatable structure 104 at a second location 250 of the first rotational surface 220, with the second location 250 lying on the first side 210 of the plane 208. In this way, the second wheel mechanism 236 can contact the bottom portion of the rotatable structure 104, with the rotatable structure 104 resting upon the second wheel mechanism 236 due to the force of gravity.

The second wheel mechanism 236 can be angularly spaced apart from the wheel mechanism 234 about the first rotational surface 220. In an example, the wheel mechanism 234 and the second wheel mechanism 236 can be spaced apart between about 60 degrees to about 120 degrees, or, in an example, between about 80 degrees to about 100 degrees. In this way, the rotatable structure 104 can be in contact with and supported by the wheel mechanism 234 and the second wheel mechanism 236 at the first rotational surface 220.

The second wheel mechanism 236 can also include a guide unit 241 including at least one second roller 252 that is configured to support and/or impart the rotation to the rotatable structure 104 about the axis 206. The second wheel mechanism 236 may also include a guide unit 241, which is similar to the guide unit 241 provided to the wheel mechanism 234, but can be configured to be installed on an opposite lateral side of the stationary unit 110 as shown in FIG. 2. As such, the guide unit 241 also includes a guide wheel 242 that can be oriented substantially perpendicular to the at least one second roller 252.

The guide wheel 242 provided to one or more of the guide units 241 described herein can rotate about a rotational axis 402 (FIG. 4) that is substantially perpendicular to a direction 404 (FIGS. 4 and 5) of linear translation of the guide wheel 242. The guide wheel 242 provided to the second wheel mechanism 236 can contact and/or engage the peripheral surface 245 at the first end 202 of the rotatable structure 104. In this way, the guide wheel 242 of the second wheel mechanism 236 can also serve to limit movement of the rotatable structure 104 in the axial direction 244 along the axis 206. For example, the guide wheel 242 can limit unintended movement of the rotatable structure 104 along the first direction 244 that is substantially parallel to the axis 206 as described in detail below.

The wheel unit 230 can include a motor 260 that can generate the force causing rotation of the rotatable structure 104. For example, the motor 260 may be coupled to one of the rollers 240 of the wheel mechanism 234. In an example, a shaft can be attached to the motor 260 and the roller 240, such that the motor 260 can cause the shaft to rotate, which may thus cause the roller 240 to rotate. This rotation may be imparted to the rotatable structure 104, whereupon the rotatable structure 104 can rotate. In this way, the motor 260 can impart rotation to the roller 240 thus causing the rotatable structure 104 to rotate.

It will be appreciated that the wheel unit 230 is not limited to being coupled to the motor 260. Rather, in an example, rotation of the rotatable structure 104 can be imparted in other ways. For example, rotation may be imparted to the rotatable structure 104 by another type of drive mechanism, such as a belt, chain, etc., with the belt, chain, etc., engaging the rotatable structure 104 and causing rotation of the rotatable structure 104. In this way, the wheel unit 230 (e.g., comprising the wheel mechanism set 232 and a second wheel mechanism set 300 illustrated in FIG. 3) may support the rotatable structure 104 while not imparting rotating to the rotatable structure 104. Rather, the wheel unit 230 can facilitate rotation of the rotatable structure 104 relative to the wheel unit 230, while a belt, a chain, etc., can engage the rotatable structure 104 and cause the rotatable structure 104 to rotate.

Figure 3:
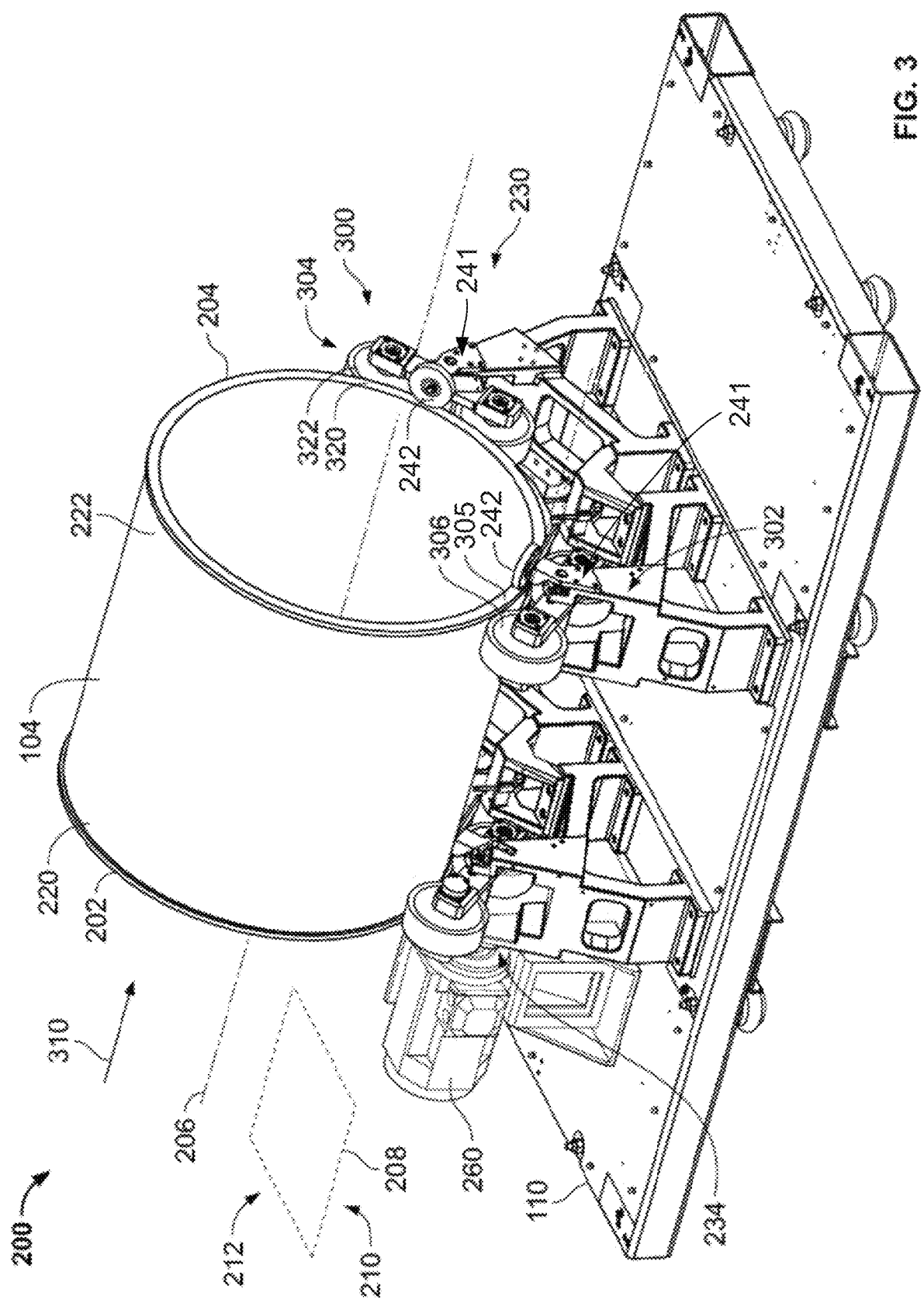
FIG. 3 is another perspective of the illustrative embodiment of the radiation system shown in FIG. 2.

Referring to FIG. 3, the second end 204 of the rotatable structure 104 is illustrated. In an example, the wheel unit 230 comprises a second wheel mechanism set 300. The second wheel mechanism set 300 is configured to at least partially support the rotatable structure 104 at the second rotational surface 222 and facilitate rotation of the rotatable structure 104 relative to the stationary unit 110. In an example, the second wheel mechanism set 300 can be supported by and/or attached to the stationary unit 110. The second wheel mechanism set 300 can be positioned adjacent to the second end 204 of the rotatable structure 104.

The second wheel mechanism set 300 comprises a third wheel mechanism 302 and a fourth wheel mechanism 304. The third wheel mechanism 302 is configured to at least partially support the rotatable structure 104 and facilitate rotation of the rotatable structure 104 relative to the stationary unit 110. In an example, the third wheel mechanism 302 can rotationally support the rotatable structure 104 at a third location 305 of the second rotational surface 222, with the third location 305 lying on the first side 210 of the plane 208. In this way, the third wheel mechanism 302 can contact the bottom portion of the rotatable structure 104, with the rotatable structure 104 resting upon the third wheel mechanism 302 due to the force of gravity.

The third wheel mechanism 302 includes at least one third roller 306 that is configured to support and/or impart the rotation to the rotatable structure 104 about the axis 206. The third wheel mechanism 302 may also include the guide unit 241, which is configured similar to the guide unit 241 provided to the wheel mechanism 234 described above. As such, the guide unit 241 also includes a guide wheel 242 that can be oriented substantially perpendicular to the at least one third roller 306. The guide wheel 242 can roll along a peripheral surface defining an aperture leading into the interior passage 207 defined by the rotatable structure 104, thereby limiting unintended movement of the rotatable structure 104 in a second axial direction 310 along the axis 206 as described in detail below.

The fourth wheel mechanism 304 is configured to at least partially support the rotatable structure 104 and facilitate rotation of the rotatable structure 104 relative to the stationary unit 110. In an example, the fourth wheel mechanism 304 can rotationally support the rotatable structure 104 at a fourth location 320 of the second rotational surface 222, with the fourth location 320 lying on the first side 210 of the plane 208. In this way, the fourth wheel mechanism 304 can contact the bottom portion of the rotatable structure 104, with the rotatable structure 104 resting upon the fourth wheel mechanism 304 due to the force of gravity.

The fourth wheel mechanism 304 can be spaced apart from the third wheel mechanism 302 along the second rotational surface 222. In an example, the third wheel mechanism 302 and the fourth wheel mechanism 304 can be angularly spaced apart between about 60 degrees to about 120 degrees, or, in an example, between about 80 degrees to about 100 degrees. In this way, the rotatable structure 104 can be in contact with and supported by the third wheel mechanism 302 and the fourth wheel mechanism 304 at the second rotational surface 222.

The fourth wheel mechanism 304 includes at least one fourth roller 322 that is configured to support and/or impart the rotation to the rotatable structure 104 about the axis 206. The fourth wheel mechanism 304 may also include the guide unit 241, which is configured similar to the guide unit 241 provided to the second wheel mechanism 236 described above. As such, the guide unit 241 also includes a guide wheel 242 that can be oriented substantially perpendicular to the at least one fourth roller 322. The guide wheel 242 can limit unintended movement of the rotatable structure 104 in a second axial direction 310 along the axis 206 as described in detail below.

Figure 4:
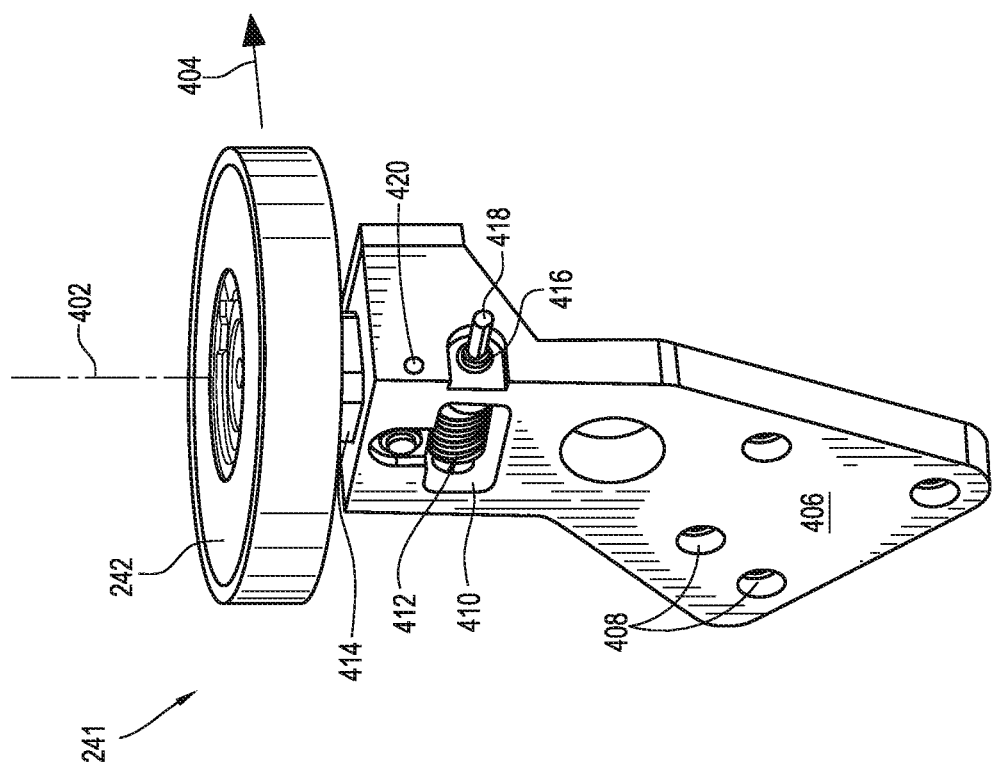
FIG. 4 is a perspective view of an illustrative embodiment of a guide unit for limiting axial movement of a rotatable structure supporting a radiation source and a detector array of a radiation system.

An illustrative embodiment of a guide unit 241 for limiting axial movement of the rotatable structure 104 is shown in FIG. 4. As shown, the guide unit 241 includes a frame member 406 configured to be supported by the stationary unit 110 of the radiation system 200. The guide member of FIG. 4 includes through holes 408 and is shaped to be mounted to one of the wheel mechanism sets, such as wheel mechanism set 232, in conjunction with the second wheel mechanism 236, for example. However, the guide unit 241 can be coupled to the stationary unit 110 by any suitable structure, and can optionally be configured substantially the same taking into account symmetry with respect to the lateral side of installation. For the sake of brevity and clarity, an embodiment of the guide unit 241 is described below in detail with reference to the wheel mechanism set 232 and the peripheral surface 245 to limit axial movement of the rotatable structure 104 in the direction 244, as shown in FIG. 2.

The frame member 406 defines an aperture 410 in which at least a portion of a wheel adjustment system 412 can be disposed. Alternate embodiments of the wheel adjustment system 412, however, can be supported externally of the frame member 406, instead of partially within the aperture 410. The wheel adjustment system 412 converts an adjustment force input by a user into the linear translation of the guide wheel 242 relative to the frame member, toward the peripheral surface 245 of the rotatable structure 104 supported by the stationary unit 110 of the radiation system 200. The guide wheel 242 can be linearly translated along a straight-line path in the direction 404. According to embodiments of the guide unit 241, the direction of linear translation can be substantially perpendicular to the rotational axis 402 about which the guide wheel 242 rotates as it travels along the peripheral surface 245 during rotation of the rotatable structure 104. According to alternate embodiments, the wheel adjustment system 412 can linearly translate the guide wheel 242 in an axial direction, which is parallel to the rotation of axis 206 of the rotatable structure 104, toward the peripheral surface 245 of the rotatable structure 104.

The guide wheel 242 is supported by a hub 414, which couples the guide wheel 242 to the frame member 406. The hub 414 can include a bearing 502 (FIG. 5) or other suitable device that allows the guide wheel 242 to pivot or rotate freely (e.g., lacks a constraint on the angular motion of the guide wheel 242) about the rotational axis 402, and roll along the peripheral surface 245 as the rotatable structure 104 is rotated about the axis 206 during operation of the radiation system 200. As described below, the hub 414 is coupled to the wheel adjustment system 412, which linearly translates the hub 414, and accordingly the guide wheel 242, relative to the frame member 406 toward the peripheral surface 245 of the rotatable structure.

Figure 5:
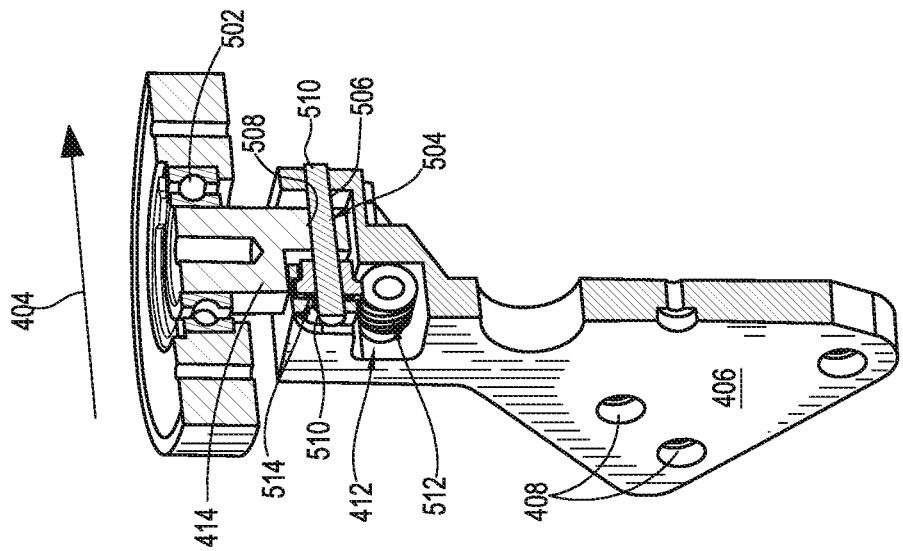
FIG. 5 is a partially-cutaway view of the embodiment of the guide unit shown in FIG. 4.

The embodiment of the wheel adjustment system 412 shown in FIGS. 4 and 5 limits the linear translation of the guide wheel 242 to translations in a fixed direction. In other words, there may be no tangential movement of the guide wheel 242 during linear translation. For example, the wheel adjustment system 412 can limit linear translation of the guide wheel 242 to only the axial direction 404, toward the peripheral surface 245, parallel with the axis 206 of the rotatable structure 104.

To achieve such linear translation of the guide wheel 242, the wheel adjustment system 412 can include a track defining the linear path along which the hub 414 supporting the guide wheel 242 is permitted to travel. For example, the track can include a threaded shaft 504 supported by a portion of the frame member 406. The threaded shaft 504 can optionally be coupled to the frame member 406 in a manner that allows free rotation of the threaded shaft 504. To be freely rotatable, the threaded shaft 504 can lack a constraint, other than the limits to the range of translation of the hub 414, on the angular motion of the threaded shaft 504. For example, based on the relative threading dimensions, the length of the threaded shaft 504, etc., linear translation of the guide wheel 242 can be limited to a distance of no greater than one half (0.5 in.) of an inch of travel in one direction. A releasable fastener such as a C-clip 510, for example, can be installed on portions of the threaded shaft that protrude beyond the mounting locations of the frame member 406. In the embodiment shown in FIG. 5, an exterior surface 506 of the threaded shaft 504 includes threading that engages compatible threading provided to a surface 508 defining an interior passage defined by the hub 414. Pivotal adjustment, and optionally complete rotation of the threaded shaft 504 causes the hub 414 to travel along the threaded shaft 504 as a result of cooperation between the threading and the compatible threading. The travel of the hub 414 along the threaded shaft 504 linearly translates the guide wheel 242 toward the peripheral surface 245 of the rotatable structure 104. Of course other embodiments can utilize a linear track such as a rack-and-pinion arrangement, or any other device that allows fine, incremental or continuous linear translation of the guide wheel 242 generally toward the peripheral surface 245 of the rotatable structure 104.

A gear system, such as a worm drive, for example, can convert an angular force input by a user into a rotational force that causes pivotal adjustment of the threaded shaft 504. Referring again to FIG. 4, an access channel 416 can be formed in the frame member 406 to extend between the aperture 410 and an exterior of the frame member 406. The access channel 416 receives an adjustment member 418 comprising a distal end that cooperates with a worm 512, shown in FIG. 5. A proximate end of the adjustment member 418 protrudes from the frame member 406, where it is accessible by a user without disassembling the frame member 406 to access the wheel adjustment system 412.

The worm 512 can include a screw comprising a cylindrical segment provided with external threading. The threading of the worm 512 meshes with compatibly-sized teeth provided to a worm gear 514 during pivotal adjustment or rotation of the worm 512, causing the worm gear 514 to be pivotally adjusted or rotated. As shown in FIG. 5, the worm gear 514 can be mounted on the threaded shaft, with a fixed angular relationship with the threaded shaft. Thus, pivotal adjustment or rotation of the worm gear 514 causes pivotal adjustment or rotation of the threaded shaft 504 which, as mentioned above, causes linear translation of the guide wheel 242 toward the peripheral surface 245 of the rotatable structure 104. Because the adjustment member 418 protrudes externally of the frame member 406, the worm 512 can be pivotally adjusted or rotated by the angular input force imparted on the adjustment member 418 by a user, without requiring disassembly of the frame member 406. The worm drive thus converts rotation of the worm 512 into pivotal adjustment of the threaded shaft 504, and linear translation of the guide wheel 242.

The adjustment member 418 can optionally form a portion of the wheel adjustment system 412, or be a separate tool that is to be inserted into the access channel 416. Regardless of whether the adjustment member 418 forms a portion of the wheel adjustment system 412, it includes an elongated post having a distal end that cooperates with the worm 512, and a proximate end that protrudes from the frame member 406. Illustrative examples of the adjustment member 418 in the form of a separate tool include, but are not limited to a screwdriver, a polygon key (e.g., a "hex key"), or other such elongated tool.

Through manipulation of the wheel adjustment system, a suitable linear translation to limit axial movement of the rotatable structure 104 can be achieved. For some embodiments, suitable linear translation is achieved once the adjustment member 418 has been manipulated to cause a surface of the guide wheel 242 to be compressed against the peripheral surface 245 of the rotatable structure 104. For example, the exterior periphery of the guide wheel 242 can be compressed at least two (0.002 in.) thousandths of an inch, or at least one (0.001 in.) thousandths of an inch; up to two (0.02 in.) hundredths of an inch, or up to one (0.01 in.) hundredth of an inch, against the peripheral surface 245. Specific embodiments of the compression include compression of the exterior periphery of the guide wheel 242 approximately five (0.005 in.) thousandths of an inch, plus or minus two thousandths of an inch (±0.002 in.).

Once the guide wheel 242 has been positioned as desired via linear translation, a locking device 420 (FIG. 4) extending through a portion of the frame member 406 can be manipulated by the user. The locking device 420 interferes with further linear translation of the guide wheel 242, toward or away from the peripheral surface 245. The locking device 420 can also be accessible, to be manipulated externally of the frame member 406, without requiring disassembly of the frame member 406, or separation of the frame member 406 from the stationary unit 110. When manipulated, the locking device 420 engages a portion of the wheel adjustment system 412, and interferes with operation of the wheel adjustment system 412 to prevent further linear translation of the guide wheel 242. For example, the locking device 420 can include a set screw that is screwed into a threaded aperture 410 of the frame member 406 to make contact with a portion of the wheel adjustment system 412. According to some embodiments, the set screw can be inserted to make contact with the threaded shaft 504, thereby creating a friction fit that interferes with pivotal adjustment of the threaded shaft 504. The contact between the set screw, and optionally cooperation between components of the wheel adjustment system 412 (e.g., the worm 512 and the worm gear 514) can resist a reactionary force urging the guide wheel 242 in a linear direction away from the peripheral surface 245. For example, the reactionary force generated as a result of contact between the guide wheel 242 and the peripheral surface 245 can be resisted, thereby maintaining a position of the guide wheel 242 against the peripheral surface 245.

Figure 6:
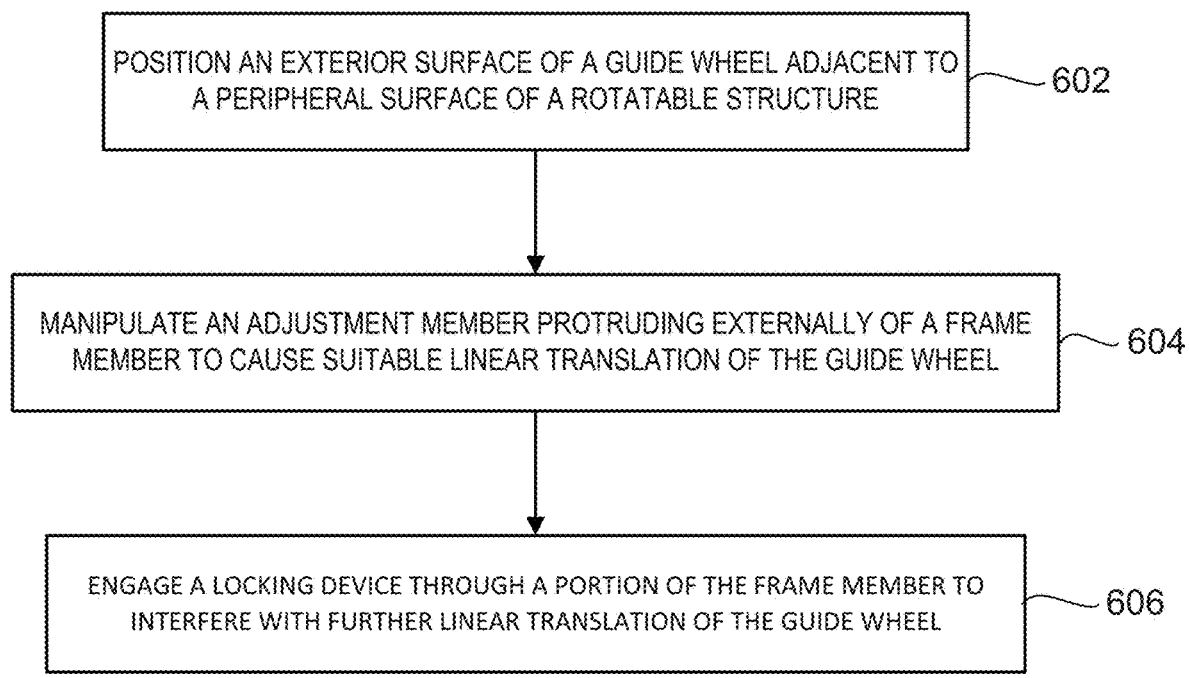
FIG. 6 is a flow diagram schematically depicting a method of limiting axial movement of a rotatable structure supporting a radiation source and a detector array of a radiation system.

A method of limiting axial movement of the rotatable structure 104 is schematically depicted by the flow diagram of FIG. 6. An exterior surface of the guide wheel 242 is positioned adjacent (e.g., within one half (0.5 in.) of an inch) to a peripheral surface of a cylindrical body of the rotatable structure 104 at block 602. Once the guide wheel 242 is so positioned, the adjustment member 418 is manipulated at block 604 to cause pivotal adjustment of the worm 512. Pivotal adjustment of the worm 512 is converted by the worm gear 514 into pivotal adjustment of the threaded shaft 504 or other mechanism to cause suitable linear translation of the guide wheel 242 toward the peripheral surface 245 of the cylindrical body of the rotatable structure 104. After manipulating the adjustment member 418 to cause suitable linear translation of the guide wheel 242, the locking device 420 is engaged by inserting a set screw or other member through a portion of the frame member 406 at block 606 to interfere with further linear translation of the guide wheel 242 away from the peripheral surface 245.

It may be appreciated that "example" and/or "exemplary" and/or "illustrative" are used herein to mean serving as an example, instance, or illustration. Any aspect, design, etc., described herein as "example" and/or "exemplary" is not necessarily to be construed as advantageous over other aspects, designs, etc. Rather, use of these terms is intended to present concepts in a concrete fashion. As used in the present disclosure, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this disclosure and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component that performs the specified function of the described component (e.g., that is functionally equivalent), even though not structurally equivalent to the disclosed structure that performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

What is claimed is:

1. A guide unit for limiting axial movement of a rotatable structure of a radiation-based imaging system, the guide unit comprising:
   a frame member;
   a guide wheel operatively coupled to the frame member and configured to rotate when the guide wheel is in contact with a periphery of a rotatable structure of a radiation-based imaging system and in response to rotation of the rotatable structure; and
   a wheel adjustment system operable to linearly translate the guide wheel in a direction transverse to an axis of rotation of the guide wheel to enable a position of the guide wheel to be adjusted relative to the periphery of the rotatable structure.

2. The guide unit of claim 1, wherein the wheel adjustment system comprises a worm drive configured to convert an angular input force into a linear translation of the guide wheel.

3. The guide unit of claim 2, wherein the worm drive comprises:
   a worm pivotally coupled to the frame member, wherein the worm is configured to pivot about a worm axis in response to the angular input force;
   a threaded shaft pivotally supported by the frame member, wherein threading of the threaded shaft engages compatible threading provided to a hub supporting the guide wheel; and
   a worm gear in threaded engagement with the worm to convert rotation of the worm into pivotal adjustment of the threaded shaft, wherein cooperation between the threading of the threaded shaft and the compatible threading of the hub is configured to cause the hub to travel along the threaded shaft, thereby linearly translating the guide wheel relative to the periphery of the rotatable structure.

4. The guide unit of claim 3, wherein the threaded shaft is supported by the frame member to be freely pivotal.

5. The guide unit of claim 1, wherein the wheel adjustment system limits a linear translation of the guide wheel to translations in a direction transverse to the axis of rotation of the guide wheel.

6. The guide unit of claim 1, wherein at least a portion of the wheel adjustment system is disposed within an aperture formed in the frame member.

7. The guide unit of claim 6, further comprising an access channel formed in the frame member, wherein the access channel extends between the aperture and an exterior of the frame member, and is configured to receive an adjustment member configured to impart an angular input force on a worm while protruding externally of the frame member.

8. The guide unit of claim 1, wherein the wheel adjustment system is configured to linearly translate the guide wheel in a direction, substantially transverse to the axis of rotation of the guide wheel, toward or away from the periphery of the rotatable structure when the guide wheel is proximate to the periphery of the rotatable structure.

9. The guide unit of claim 1, further comprising a locking device that is configured to extend through a portion of the frame member to engage a portion of the wheel adjustment system and interfere with linear translation of the guide wheel.

10. A sub-assembly of a radiation-based imaging system comprising:
    a stationary unit;
    a rotatable structure configured for rotation about an axis of rotation relative to the stationary unit, the rotatable structure comprising: (i) a cylindrical body extending in an axial direction along the axis of rotation to define an interior passage, and (ii) a peripheral surface at a terminal end of the cylindrical body, the peripheral surface defining an aperture leading into the interior passage defined by the cylindrical body; and
    a guide unit for limiting axial movement of the rotatable structure, the guide unit comprising:
      a frame member configured to be operatively coupled to the stationary unit;
      a guide wheel operatively coupled to the frame member and configured to rotate when the guide wheel is in contact with the peripheral surface of the rotatable structure and in response to rotation of the rotatable structure; and
      a wheel adjustment system operable to linearly translate the guide wheel in the axial direction to enable a position of the guide wheel to be adjusted relative to the peripheral surface of the rotatable structure.

11. The sub-assembly of the radiation-based imaging system of claim 10, wherein the wheel adjustment system comprises a worm drive configured to convert an angular input force into a linear translation of the guide wheel.

12. The sub-assembly of the radiation-based imaging system of claim 11, wherein the worm drive comprises:
    a worm pivotally coupled to the frame member, wherein the worm is configured to pivot about a worm axis in response to the angular input force;
    a threaded shaft pivotally supported by the frame member, wherein threading of the threaded shaft engages compatible threading provided to a hub supporting the guide wheel; and
    a worm gear in threaded engagement with the worm to convert rotation of the worm into pivotal adjustment of the threaded shaft, wherein cooperation between the threading of the threaded shaft and the compatible threading of the hub is configured to cause the hub to travel along the threaded shaft as a result of the pivotal adjustment of the threaded shaft, thereby linearly translating the guide wheel relative to the peripheral surface of the rotatable structure.

13. The sub-assembly of the radiation-based imaging system of claim 12, wherein the threaded shaft is supported by the frame member to be freely pivotal.

14. The sub-assembly of the radiation-based imaging system of claim 10, wherein the wheel adjustment system limits a linear translation of the guide wheel to translations in the axial direction.

15. The sub-assembly of the radiation-based imaging system of claim 10, wherein at least a portion of the wheel adjustment system is disposed within an aperture formed in the frame member.

16. The sub-assembly of the radiation-based imaging system of claim 15, wherein the guide unit further comprises an access channel formed in the frame member, wherein the access channel extends between the aperture of the frame member and an exterior of the frame member, and is configured to receive an adjustment member that is configured to impart an angular input force on a worm while protruding externally of the frame member.

17. The sub-assembly of the radiation-based imaging system of claim 10, wherein the guide unit further comprises a locking device comprising a member that is configured to extend through a portion of the frame member and engage a portion of the wheel adjustment system to interfere with linear translation of the guide wheel.

18. The sub-assembly of the radiation-based imaging system of claim 10, wherein the guide wheel is rotatable about a rotational axis that is substantially perpendicular to the axial direction.

19. A method of limiting axial movement of a rotatable structure of a radiation-based imaging system, the method comprising:

supporting a rotatable structure of a radiation-based imaging system, configured to rotate about an axis of rotation, above a stationary unit;

linearly translating a position of a guide wheel in a direction transverse to an axis of rotation of the guide wheel to enable a position of the guide wheel to be adjusted relative to a periphery of the rotatable structure, the guide wheel operatively coupled to the stationary unit relative to a peripheral surface of the rotatable structure such that the guide wheel contacts the peripheral surface to limit axial movement of the rotatable structure; and after linearly translating the position of the guide wheel, locking the position of the guide wheel.

20. The method of claim 19, wherein adjusting the position of the guide wheel comprises causing compression of a surface of the guide wheel up to two hundredths of an inch (0.02 in.) against the peripheral surface of the rotatable structure.

21. The method of claim 19, wherein adjusting the position of the guide wheel comprises linearly translating the guide wheel a distance of up to one half of an inch (0.5 in.).

22. The method of claim 19, wherein linearly translating the position of the guide wheel further comprises linearly translating the guide wheel in an axial direction of the rotatable structure.

* * * * *